(12) United States Patent
Mestroni et al.

(10) Patent No.: US 7,169,948 B2
(45) Date of Patent: Jan. 30, 2007

(54) ANIONIC AND NEUTRAL COMPLEXES OF RUTHENIUM (II) WITH NITROGEN OXIDE

(75) Inventors: Giovanni Mestroni, Trieste (IT); Enzo Alessio, Trieste (IT); Gianni Sava, Trieste (IT); Alberta Bergamo, Trieste (IT)

(73) Assignee: Sigea S.R.L., Trieste (IT)

( * ) Notice: Subject to any disclaimer, the term of this patent is extended or adjusted under 35 U.S.C. 154(b) by 395 days.

(21) Appl. No.: 10/472,834

(22) PCT Filed: Mar. 22, 2002

(86) PCT No.: PCT/EP02/03256

§ 371 (c)(1),
(2), (4) Date: Sep. 22, 2003

(87) PCT Pub. No.: WO02/076998

PCT Pub. Date: Oct. 3, 2002

(65) Prior Publication Data

US 2004/0106799 A1 Jun. 3, 2004

(51) Int. Cl.
*C07F 15/00* (2006.01)
*A61K 31/28* (2006.01)
*C01G 55/00* (2006.01)

(52) U.S. Cl. ............... 556/137; 548/101; 548/108; 546/2; 514/492; 423/22

(58) Field of Classification Search ............... 556/137; 514/492; 423/22; 548/101, 108; 546/2
See application file for complete search history.

(56) References Cited

OTHER PUBLICATIONS

Rudnitskaya et al., Russian Journal of Coordination Chemistry, vol. 23, No. 9, pp. 658-661 (1997).*
Inorganica Chimica Acta, 160 (1989) p. 59-63; Reactions of Ruthenium (III) Chlorocomplexes with Nitrogen Oxides N0 and N02.
Inorganic Chemistry Laboratories; I.P. Evans et al.; p. 204-209; "Dichlorotetrakis (dimethyl sulphoxide) ruthenium (II) and its Use as a Source Material for Some New Ruthenium (ii) Complexes".
Haya/Interperodica Publishing; 1997; O.V. Rudnitskaya et al.; Interaction of Ruthenium Nitroso Complexes with Dimethyl Sulfoxide.

* cited by examiner

*Primary Examiner*—Porfirio Nazario-Gonzalez
(74) *Attorney, Agent, or Firm*—Stetina Brunda Garred & Brucker

(57) ABSTRACT

A class of anionic and neutral complexes of ruthenium (II) containing nitrogen oxide (NO) and optionally a nitrogen ligand is described; a process for their preparation is also described. The preparation process includes the use of starting complexes of ruthenium (III) which are reacted with suitable reagents so as to obtain complexes containing NO coordinated to ruthenium (II). Additional substitution reactions allow the introduction of new groups that coordinate to the ruthenium atom, among which some nitrogen ligands.

46 Claims, No Drawings

ANIONIC AND NEUTRAL COMPLEXES OF RUTHENIUM (II) WITH NITROGEN OXIDE

FIELD OF THE INVENTION

The present invention relates the field of metal complexes; the invention concerns new anionic and neutral complexes of ruthenium (II) containing nitrogen oxide (NO) and their preparation process.

STATE OF THE ART

Numerous ruthenium complexes are described in literature with regard to studies on their structural, electrochemical and photophysical properties as well as their pharmacological activity.

Various anionic complexes of ruthenium have been tested for their antitumor activity ((ImH)[trans-RuCl$_4$Im$_2$]: B. K. Keppler et al., J. Cancer Res. Clin. Oncol., 111: 166–168, 1986, Na[trans-RuCl$_4$(Me$_2$SO)(L)] where L=nitrogen ligand: WO90/13553), and have been shown to be effective in slowing down the growth of primary tumours. More recent complexes of type (LH)[trans-RuCl$_4$(Me$_2$SO)(L)] (WO98/00431) possess strong antimetastatic activity.

Various dimeric complexes of ruthenium are also known. Among these, some cationic complexes characterized by the presence of nitrogen bridging ligands (for example, heterocyclic compounds, pyridine rings) have been studied for their electrochemical and photophysical properties (Creutz et al. Journal Am. Chem. Soc., 21, 1086, 1973), while some neutral and anionic complexes have been described for their antitumoral activity (PCT/EP00/03484). The synthesis and characterisation of complexes comprising nitrogen ligands and the nitrosyl ion is reported in literature (S. Bohle et al. Eur. J. Inorg. Chem., 1609, 2000).

The above described ruthenium complexes exert their antitumour activity by releasing one or more of their ligands and covalently binding to biological targets. Therefore, most ruthenium complexes endowed with antitumour activity are reactive and selectively labile species and are hydrolised in aqueous solution, in particular at physiological pH.

In the last few years many efforts have been have been made towards the development of new ruthenium complexes endowed with antitumor activity and characterised by an improved inertness.

SUMMARY OF THE INVENTION

Object of the present invention are a class of anionic and neutral complexes of ruthenium (II) containing nitrogen oxide (NO) and optionally also a nitrogen ligand. The complexes of the invention are surprisingly inert in acqueous solution at both pH 5.5. and 7.4. Notwithstanding their high inertness, the complexes of the invention are also endowed with a cytotoxicity surprisingly higher than that of ruthenium complexes of the prior art, for example those of International Patent Application WO98/00431.

Therefore, the complexes of the present invention are useful for the preparation of a medicament for the therapy of tumoural or hyperproliferative pathologies.

A further object of the present invention is a process for the preparation of the above complexes of the invention. Said process comprises the reaction of complexes of ruthenium (III) with suitable reagents so as to obtain complexes containing NO coordinated to ruthenium (II). Additional substitution reactions allow the introduction of other groups coordinated to the ruthenium atom, among which some nitrogen ligands.

In the presence of suitable nitrogen ligands the above process also allows to obtain dimeric complexes of ruthenium containing NO.

Therefore, the complexes of the present invention are useful as intermediates for the preparation of additional ruthenium complexes.

DETAILED DESCRIPTION OF THE INVENTION

The compounds object of the present invention are anionic or neutral complexes of ruthenium (II) of formula (I):

wherein:
A represents a halogen chosen from the group consisting of Cl$^-$ and Br$^-$
W represents NO$^+$
M represents SOR$_1$R$_2$
P represents NR$_3$R$_4$R$_5$ or LRuA$_a$M$_m$W
a is a whole number between 3 and 4
m is a whole number between 0 and 2
p is a whole number between 0 and 1
r can be 0,–1,–2
being a+m+p=5 wherein:
R$_1$ and R$_2$ are identical or different from each other and represent C$_{1–6}$ alkyl, C$_3$–C$_7$ cycloalkyl, phenyl and aryl, or R$_1$ and R$_2$ form together with the sulphur atom a 5–7 term heterocyclic ring;
R$_3$, R$_4$ and R$_5$ are identical or different from each other and represent hydrogen, saturated or unsaturated C$_1$–C$_6$ linear or branched alkyl C$_3$–C$_7$ cycloalkyl, phenyl and aryl, or NR$_3$R$_4$R$_5$ is a saturated or unsaturated 5–7 term nitrogen heterocyclic compound, optionally containing at least one additional eteroatom chosen from O, S, N, the latter being optionally substituted with a C$_1$–C$_4$ alkyl, aryl or benzyl residue, said nitrogen heterocyclic compound being optionally benzocondensed and/or substituted with C$_1$–C$_4$ alkyl, C$_1$–C$_4$ alkoxyl, C$_1$–C$_4$ alkylthio, benzyl or aryl;
L represents a heterocyclic ligand containing at least two heteroatoms whose electron pairs are involved in the bond with the two ruthenium atoms present in the complex.
Preferably, in the complexes of the invention A is chloride (Cl$^-$).

In the complexes of the invention, the coordination of the molecule W=NO occurs formally as a nitrosyl ion: NO$^+$ and means that the state of formal oxidation of ruthenium in the products is 2+; in fact the products are diamagnetic, whereas the starting compounds are paramagnetic.

In the complexes of the invention of formula (I) the group M=SOR$_1$R$_2$ is preferably represented by dimethylsulphoxide (R$_1$=R$_2$=methyl), diethylsulphoxide (R$_1$=R$_2$=ethyl), tetramethylenesulphoxide (R$_1$ and R$_2$ form a 5 term ring with the sulphur atom). The bond between the sulphoxide and ruthenium always occurs through the oxygen atom (SOR$_1$R$_2$) when the sulphoxide is trans to the NO$^+$.

In the complexes of the invention of formula (I) the nitrogen atom present in the nitrogen ligand P=NR$_3$R$_4$R$_5$ makes the electron pair available for the formation of the coordination bond with the ruthenium atom. In particular, the R$_3$, R$_4$, R$_5$ groups can be identical or different from each other and are chosen in the group consisting of H, saturated or unsaturated $C_1$–$C_6$ linear or branched alkyl, $C_3$–$C_7$ cycloalkyl, phenyl or aryl.

When $NR_3R_4R_5$ is a 5-member nitrogen heterocyclic compound it is preferably chosen from the group consisting of imidazole, N-methylimidazole, pyrazole and oxazole; even more preferably, said nitrogen heterocyclic compound is imidazole.

When $NR_3R_4R_5$ is a 6-member heterocyclic compound, it is preferably chosen from the group consisting of pyridine, 3,5-lutidine and 4-methyl-pyridine.

When $NR_3R_4R_5$ is a 7-member heterocyclic compound, it is preferably chosen from the group consisting of azepine, diazepine and oxazepine.

Lastly, when said heterocyclic compound is benzocondensed, it is preferably chosen in the group consisting of indazole, isoquinoline, benzimidazole and 1,5,6-trimethyl-benzimidazole.

In the complexes of the invention of formula (I) the heterocyclic ligand L present in the group $P=LRuA_aM_mW$ always contains two nitrogen atoms that are coordinated through their electron pairs with the two ruthenium atoms of the complex of formula (I). Such nitrogen atoms can be on the same heterocyclic ring or on two separate heterocyclic rings. In the latter case, the ligand L assumes the structure B'-X-B", where B' and B" represent the two nitrogen heterocyclic compounds that are coordinated with the two ruthenium atoms, and X represents —COO—, —O—, —$(CH_2)_n$—, —$(CH=CH)_n$—, -(aryl)$_n$-, -(heterocyclic compound)$_n$-, —CH=CH-Phe-CH=CH—, —$(C≡C)_n$—, where n is between 0 and 4.

The heteroaromatic or aromatic rings contained in the structure B'-X-B" can be condensed or uncondensed and substituted with a group chosen from alkyl groups having from 1 to 6 carbon atoms (the methyl and ethyl groups are preferred), $C_1$–$C_4$ alkoxy, phenyl groups, CN and $NO_2$.

Examples of uncondensed heteroaromatic rings are: pyrrole, imidazole, pyrazole, pyrazine, pyrimidine, pyridine.

Examples of condensed heteroaromatic rings are: quinoline, isoquinoline, carbazole.

Examples of condensed aromatic rings are: naphthalene, anthracene, phenanthrene.

Preferred examples of B'-X-B", whose structure is shown below, are:

4,4'-bipyridyl (B'=B"=pyridine, X=—$(CH_2)_n$—, where n=0), bis-imidazole (B'=B"=imidazole, X=—$(CH_2)_n$— where n=0)

1,2-bis(4-pyridyl)ethane (B'=B"=pyridine, X=—$(CH_2)_6$— where n=2), 1,2-bis(4-pyridyl)propane (B'=B"=pyridine, X=—$(CH_2)_n$— where n=3), trans-1,2-bis(4-pyridyl)ethylene (B'=B"pyridine, X=—$(CH=CH)_n$— where n=1).

When formula (I) represents an anionic species (i.e. r=−1, − 2) then a cation (Q) must be present. Said cation (W) is preferably a proton bound to a base (e.g. $(Me_2SO)_2H^+$) or is chosen from the group consisting of alkaline or alkaline-earth metals, cations of formula $^+NR_3R_4R_5R_6$ where $R_3$, $R_4$, $R_5$, $R_6$ are identical or different to each other and represent hydrogen, saturated or unsaturated $C_1$–$C_6$ linear or branched alkyl, $C_3$–$C_7$ cycloalkyl, phenyl and aryl, or where $^+NR_3R_4R_5R_6$ is to a saturated or unsaturated 5–7 term nitrogen heterocyclic compound, optionally containing at least one eteroatom chosen from O, S, N, the latter being optionally substituted with a $C_1$–$C_4$ alkyl, aryl or benzyl residue, said nitrogen heterocyclic compound being optionally benzocondensed and/or substituted with $C_1$–$C_4$ alkyl, $C_1$–$C_4$ alkoxyl, $C_1$–$C_4$ alkylthio, benzyl or aryl.

The preferred meanings of Q are $Na^+$, $K^+$, $NH_4^+$, $Net_4^+$ (tetraethylammonium), $Nbu^+$ (tetrabutylammonium), $ImH^+$ (imidazole).

In the anionic complexes of formula (I) having P represented by $NR_3R_4R_5$ Q is preferably $^+NR_3R_4R_5R_6$ with $R_6$=H and $R_3$, $R_4$, $R_5$ having the same meaning as $R_3$, $R_4$, $R_5$ present in P.

Ruthenium complexes particularly preferred according to the present invention are salts of anionic complexes of formula (I) wherein A=Cl, M=$Me_2SO$, W=NO, a=4, m=1, p=0, r=−1 and are salts of anionic complexes of formula (I) wherein A=Cl, P=imidazole, W=NO, a=4, m=0, p=1, r=−1.

The metal complexes may contain crystallization molecules like $SOR_1R_2$, acetone nitromethane or water.

The complexes of the invention have the advantage of being stable. In fact, the coordination bond between ruthenium and W=$NO^+$ is very stable and the nitrogen oxide does not free itself easily from the complex. Furthermore, in the complexes having also an M represented by $SOR_1R_2$ also said sulphoxide ligand is stable.

An additional object of the present invention is the process for the preparation of the ruthenium complexes of formula (I) described above.

The process of the invention may comprise a single step (Step 1) or two steps (Step 1 and Step 2).

Step 1: The starting complex $[Ru^{III}A_4M_2]^{-1}$ or $[Ru^{III}A_3M_3]$, where A and M have the same meanings described for the complex of formula (I), is dissolved in suitable organic solvents or mixtures thereof (e.g. dichloromethane, chloroform, acetone, acetone and DMSO, DMSO, nitromethane, water). Gaseous NO or a suitable NO generating reagent, is added to this solution for a period of time between 15 minutes and 5 hours, preferably between 1 and 2 hours, and the reaction is allowed to occur for a period of time between 30 min and 24 hours, preferably between 1 and 4 hours, at a temperature of between 0 and 200° C., preferably between 15 and 150° C. The reaction leads to the a corresponding anionic or neutral complex containing the W group of formula $[Ru^{II}A_4M_1W]^{-1}$ or $[Ru^{II}A_3M_2W]$.

Step 2: The complex obtained at step 1 can be subsequently modified by reaction with P in suitable organic solvents or mixtures thereof (e.g. dichloromethane, chloroform, acetone, acetone and DMSO, DMSO, nitromethane) for a period of time between 15 min and 5 hours, preferably between 1 and 4 hours and at a temperature between 0 and 150° C. After isolation and purification a complex of formula $[RuA_4P_1W]^{-1}$ or $[RuA_3M_1P_1W]$ is obtained. The reaction also allows the preparation of the complex $[RuA_3P_2W]$.

The above described two-step reaction process allows to obtain symmetrical or asymmetrical anionic or neutral dimeric complexes of ruthenium (II) with $NO^+$, for example dimers of formula: $[(RuA_4W)_2L]^{-2}$, $[RuA_3MW)_2L]$, $[(RuA_4W)(LRuA_3MW)]_{-1}$. Alternatively, symmetrical dimers of the complexes of the invention can also be obtained through a two-step process comprising Step 1 followed by Step 3.

Step 3 consists of the reaction between the products of step 1, $[Ru^{II}A_4M_1W]^{-1}$ or $[Ru^{II}A_3M_2W]$ with ½ equivalent of L.

The gaseous nitrogen oxide (NO) used in the processes described above can be flushed into the reaction vessels directly from a cylinder containing said gas. Alternatively, nitrogen oxide can be generated by decomposition of nitrites. The oxide can thus be first produced by dripping concentrated sulphuric acid onto NaNO$_2$ and then bubbled through a saturated aqueous solution of NaOH before conveying it to the reaction vessel. Alternatively, as regards the in situ production of nitrogen oxide, organo-nitrosyl reagents can be used such as MeN(NO)(CONH$_2$), Et$_2$NNO, Cl$_3$CNO. The nitrogen oxide can be added to the starting ruthenium complex directly as the nitrosyl ion NO$^+$, usually as NOBF$_4$ or NOPF$_6$. Said complexes can be used as starting products for the preparation of other ruthenium complexes comprising the nitrosyl group.

Although they are more inert, the ruthenium complexes of the invention have a more pronounced antiproliferative and cytotoxic activity compared with that of the ruthenium complexes of the prior art such as the compounds of formula LH[trans-RuCl$_4$(Me2SO)(L)] and are suitable for use in the treatment hyperproliferative or tumoral pathologies.

Therefore, a further object of the present invention is the use of the ruthenium complexes of the invention as active agents in the manufacture of a medicament for the treatment of tumoral and hyperproliferative pathologies, such as, for example, cancer, psoriasis and rheumatoid arthritis.

A further object of the present invention are pharmaceutical compositions comprising a therapeutically effective amount of at least one of the ruthenium complexes of the invention in combination with suitable pharmaceutically acceptable excipients and/or diluents.

The invention will be better understood with reference to the following examples that are provided for illustrative, non-limiting purposes.

EXPERIMENTAL PART

Example 1

Preparation of the complex [(Me$_2$SO)$_2$H][trans-Ru$^{II}$Cl$_4$(Me$_2$SO—O)NO] corresponding to formula (I) with A=Cl, M=Me$_2$SO, W=NO, a=4, m=1, p=0, r=−1.

1.2 g of [(Me$_2$SO)$_2$H][trans-Ru$^{III}$Cl$_4$(Me$_2$SO—S)$_2$] (1.44 mmol) (E. Alessio et al, Inorg. Chem., 30,609,1991) are dissolved in 1.3 ml of Me$_2$SO and 31 ml of acetone in a 100 ml flask. The orange solution is kept under magnetic agitation under a nitrogen oxide flow for 2 hours and afterwards is left under agitation in NO atmosphere overnight. The suspension obtained is vacuum-filtered and the purple solid recovered is washed first with cold acetone and then with ethyl ether and vacuum dried. Additional fraction of products are obtained from the mother waters.

Total yield: 0.80 g (73%). MW 508.28. C$_6$H$_{19}$N$_1$Cl$_4$O$_4$S$_3$Ru$_1$]. [Elementary Analysis-theoretical: % C 14.18, % H 3.77, % N 2.76, experimental: % C 14.1, % H 3.72, % N 2.92. Spectrum $^1$H-NMR (ppm) D$_2$O:Ru(II)—Me$_2$SO—O 2.95 (s, 6H), Me$_2$SO 2.71 (s, 12H). IR spectrum (KBr, cm$^{-1}$): ν (N≡O) 1864, ν (S—O) 924, ν [(Me$_2$SO)$_2$H] 725, ν (Ru—O) 501. The structure was ascertained by X-ray.

Example 2

Preparation of the complex [NBu$_4$][trans-Ru$^{II}$Cl$_4$ (Me$_2$SO—O)NO], corresponding to formula (I) with A=Cl, M=Me$_2$SO, W=NO, a=4, m=1, p=0, r=−1.

A solution of 0.278 g (1.00 mmol) of tetrabutylammonium chloride in 1.4 ml of water is added to a red solution of 0.252 g of [(Me$_2$SO$_2$H][trans-Ru$^{III}$C$_4$(Me$_2$SO—O)NO] (0.496 mmol) in 2 ml of water. After the addition, a dark pink precipitate is formed which is vacuum-filtered, washed first with a little cold acetone, then with ethyl ether and vacuum dried. Yield: 0.226 g (77%). MW 593.484. [C$_{18}$H$_{42}$N$_2$Cl$_4$O$_2$S$_1$Ru$_1$].

Elementary Analysis-theoretical: % C 36.42, % H 7.13, % N 4.72, experimental: % C 36.6, % H 7.21, % N 4.67. $^1$H-NMR spectrum (ppm) CD$_3$NO$_2$:Ru(II)—Me$_2$SO—O 2.91 (S, 6H), Bu$_4$N 3.25 (m, 8H), 1.67 (m, 8H), 1.46 (m, 8H), 1.02 (t, 12H). IR spectrum (KBr, cm$^{-1}$): ν (N≡O) 1867, (S—O) 937, ν (Ru—O) 501.

Example 3

Preparation of the complex [ImH][trans-Ru$^{III}$Cl$_4$(Me$_2$SO)$_2$]

0.5 g of the complex [(Me$_2$SO)$_2$H][trans-Ru$^{III}$Cl$_4$(Me$_2$SO)$_2$] (1 mmol) are dissolve 23 ml of ethanol and 0.3 ml of H$_2$O. 188 mg of solid ImHCl (1.8 mmol) are added to the solution under stirring. The product immediately precipitates as a red-orange coloured microcrystalline solid, which is directly vacuum-filtered, washed with cold ethanol, cold acetone and ethyl ether and vacuum dried. Yield: 0.35 g (75%). MW 468.22 [C$_7$H$_{17}$N$_2$Cl$_4$O$_2$RuS$_2$].

Elementary Analysis-theoretical: % C 17.9, % H 3.65, % N 5.98, experimental: % C 18.1, % H 3.67, % N 5.94. The UV-vis, NMR spectra confirm the presence of the anion [trans-RuCl$_4$(Me$_2$SO)$_2$]$^-$ and of the cation ImH$^+$.

Example 4

Preparation of the complex [ImH][trans-Ru$^{II}$Cl$_4$(Me$_2$SO—O)NO], corresponding to formula (I) with A=Cl, M=Me$_2$SO, W=NO, a=4, m=1, p=0, r=−1.

The synthesis is similar to that of [(Me$_2$SO)$_2$H][trans-Ru$^{II}$Cl$_4$(Me$_2$SO—O)NO]. 0.5 g of [ImH][trans-Ru$^{III}$/Cl$_4$(Me$_2$SO—S)$_2$] (1.07 mmol) are suspended in 10 ml of nitromethane. NO is bubbled through for 2 hours and a dark red solution is obtained. The solvent is removed and the oil obtained is recovered with acetone. The dark pink product that forms is vacuum-filtered, washed first with cold acetone, then with ethyl ether and vacuum dried.

Yield: 0.134 g (30%). MW 420.10 [C$_5$H$_{11}$N$_3$Cl$_4$O$_2$S$_1$Ru$_1$]. Elementary Analysis-theoretical: % C 14.29, % H 2.64, % N 10.0, experimental: % C 14.1, % H 2.49, % N 10.20. $^1$H-NMR spectrum (ppm) D$_2$O: ImH 8.59 (s, 1H), 7.45 (s, 2H); Ru(II)—Me$_2$SO—O 2.77 (s, 6H), IR spectrum (KBr, cm$^{-1}$): ν (N≡O) 1864, ν (S—O) 922, (ImH) 626, ν (Ru—O) 501.

Example 5

Preparation of the complex [mer-Ru$^{II}$Cl$_3$(Me$_2$SO—O)$_2$NO], corresponding to formula (I) with A=Cl, M=Me$_2$SO, W=NO, a=3, m=2, p=0, r=0. A solution of 0.30 g of [mer-Ru$^{III}$Cl$_3$(Me$_2$SO—S)$_2$ (Me$_2$SO—O)] (E. Alessio et al, Inorg. Chem., 1991, 30,609) in 6 ml of dichloromethane is kept under agitation and under a NO flow for approximately 2 hours. After one hour the formation of a reddish solid is observed. The product is vacuum-filtered, washed with a little dichloromethane/ethyl ether and vacuum dried.

Yield: 0.176 g (65.8%). MW 393.69. [C$_4$H$_{12}$N$_1$Cl$_3$O$_3$S$_2$Ru$_1$]. Elementary Analysis-theoretical: % C 12.2, % H 3.08, % N 3.56, experimental: % C 12.1, % H 2.85, % N 3.58. Spectrum $^1$H-NMR (ppm) CD$_3$NO$_2$: Ru(II) Me$_2$SO—O 2.97 (s, 6H), 2.91 (s, 6H). IR spectrum (KBr, cm$^{-1}$): ν (N—O) 1878, ν (S—O) 928, 898, ν (Ru—O) 503, 492. The structure was ascertained by X-ray.

Example 6

Preparation of the complex [Nbu$_4$][trans-Ru$^{II}$Cl$_4$(Im)NO], corresponding to formula (I) with A=Cl, P=imidazole, W=NO, a=4, m=0, p=1, r=−1.

0.110 g of [Nbu$_4$][trans-Ru$^{II}$Cl$_4$(Me$_2$SO—O)NO] (0.18 mmol) are dissolved in 5 ml of acetone. 0.050 g of imidazole (0.74 mmol) are added to the solution. The solution is refluxed for 3 hours. After approximately one hour the solution changes its colour from pink to red. The solution is allowed to cool and a dark red microcrystalline precipitate is formed that is vacuum-filtered, washed first with cold acetone, then with ethyl ether and vacuum dried. Yield: 0.036 g (33.6%). MW 583.43. [C$_2$H$_{40}$N$_4$Cl$_4$O$_1$Ru$_1$].

Elementary Analysis Theoretical: % C 39.71, % H 6.91, % N 9.60, experimental: % C 39.6, % H 7.06, % N 9.75. Spectrum $^1$H-NMR (ppm) CD$_3$NO$_2$: Im 8.32 (s, 1H), 7.5 (s, 1H), 7.2 (s, 1H), Bu$_4$N 3.26 (m, 8H), 1.70 (m, 8H), 1.40 (m, 8H), 0.96 (t, 12H). IR spectrum (KBr, cm$^{-1}$): ν (N=O) 1861.

Example 7

Preparation of the complex [Im$_2$H][trans-Ru$^{II}$Cl$_4$(Im)NO], corresponding to formula (I) with A=Cl, P=Imidazole, W=NO, a=1, m=0, p=1, r=−1.

0.150 g of [ImH][trans-Ru$^{II}$Cl$_4$(Me$_2$SO—O)NO] (0.36 mol) are dissolved in 15 ml of acetone, 0.1 g of imidazole (1.5 mmol) are added. The solution is refluxed for 3 hours. After approximately 1.5 hours the solution changes its colour from an initial pink colour to red. The solution is allowed to cool and the solvent is removed and the oil obtained is recovered with approximately 2 ml of nitromethane. A red microcrystalline precipitate is formed that is vacuum-filtered, washed first with cold nitromethane, then with ethyl ether and vacuum dried. MW 478.13. [C9H13N7Cl14O1Ru1].

Elementary Analysis-theoretical: % C 22.6, % H 2.74, % N 20.5, experimental: % C 22.4, % H 2.62, % N 20.1. $^1$H-NMR spectrum (ppm) D2O: Im 8.39 (s, 1H), 7.56 (s, 1H), 7.23 (s, 1H), ImH 8.23 (s, 2H), 7.31 (s, 4H). IR spectrum (KBr, cm−1): ν (N≡O) 1873, (Im) 1064, 652, 619, (ImH) 609.

Example 8

Preparation of the complex [trans,cis,cis-Ru$^{II}$Cl$_2$(Me$_2$SO—O)$_2$(NO)NO$_2$].

The solution of 0.20 g of [trans-Ru$^{II}$Cl$_2$(Me$_2$SO—S)$_4$] (E. Alessio et al, Inorg. Chem., 1988, 27, 4099–4106) in 8 ml of dichloromethane is placed under agitation and under a NO flow for approximately 1 hour. The solution changes its colour from yellow to a deep red. The formation of an orange solid is observed after a few hours. The product is vacuum-filtered, washed first with a little dichloromethane, then with ethyl ether ether and vacuum dried.

Yield: 0.096 g (56.9%). MW 404.24. [C$_4$H$_{12}$N$_2$Cl$_2$O$_5$S$_2$Ru$_1$]. Elementary Analysis-theoretical: % C 1.88, % H 2.99, % N 6.93, experimental: % C 11.8, % H 2.69, % N 6.51. $^1$H-NMR spectrum (ppm) CD$_3$NO$_2$: Ru(II)—Me$_2$SO—O 2.98 (s, 6H), 2.81 (s, 6H). IR spectrum (KBr, cm$^{-1}$): ν (N≡O) 1906, ν (S—O) 916, ν (Ru—O) 499, 486, ν (NO$_2$) 1328, 1314, δ (NO$_2$) 825. The structure was ascertained by X-ray.

The same product is obtained with a yield of 34.5% using [cis-RuCl$_2$(Me$_2$SO)$_4$] as the starting compound.

Example 9

The cytotoxicity of the ruthenium complexes prepared in Example 4 and 7 was tested on two significative tumor cell lines: MCF-7, a human hormone dependent mammary carcinoma cell line and TS/A, a murine adenocarcinoma cell line.

At day 0 4000 TS/A cells and 5000 MCF-7 cells were sown in 96-welled dishes in 200 μl of culture medium. The culture medium used was RPMI medium supplemented with 10% FCS for the TS/A line and a mixture 1:1 of DMEM and is F12 medium supplemented with 10% FCS for MCF-7. At day 1 the culture medium was removed and substituted with an identical medium containing 5% FCS only (control) or 5% FCS and the test compound (complex of example 4 or example 7) at the following concentrations: 0.1 μM, 1 μM, 3 μM, 10 μM, 30 μM, 100 μM, 300 μM, 600 μM and 1000 μM.

After 24, 48 and 72 hours cell viability was evaluated with a MTT test. The IC50 concentrations calculated for both cell lines are shown in the following table:

|  | TSA | | | MCF-7 | | |
| --- | --- | --- | --- | --- | --- | --- |
|  | 24 hours | 48 hours | 72 hours | 24 hours | 48 hours | 72 hours |
| Complex of Ex. 4 | 155 μM | 20 μM | 17 μM | 764 μM | 118 μM | 26 μM |
| Complex of Ex. 7 | 141 μM | 39 μM | 33 μM | 532 μM | 143 μM | 18 μM |

The results obtained show that both the ruthenium complexes tested exert a cytotoxic and antiproliferative action. Although murine cells are more sensitive towards the cytotoxic and antiproliferative activity of the compounds tested for short contact times, no difference between human and murine cells is observed for prolonged contact times.

The cytotoxic activity of the Ruthenium complexes tested is significantly higher compared with that of similar compounds of the prior art, such as LH[trans-RUCl$_4$(Me$_2$SO)(L)].

The invention claimed is:

1. A neutral ruthenium (II) complex of formula (I) or a salt of an anionic ruthenium complex of formula (I) with cations Q:

wherein:
A represents a halogen chosen form the group consisting of Cl$^-$ and Br$^-$
W represents NO$^+$
M represents SOR$_1$R$_2$
P represents NR$_3$R$_4$R$_5$, or LRuA$_a$M$_m$W
a is a whole number between 3 and 4
m is a whole number between 0 and 2 p is a whole number between 0 and 1
r can be 0, −1, −2
being a+m+p=5
wherein:
$R_1$ and $R_2$ are identical or different from each other and represent $C_1$–$C_6$ alkyl, $C_3$–$C_7$ cycloalkyl, phenyl or aryl, or $R_1$ and $R_2$ form a 5–7 term heterocyclic ring together with the sulphur atom;
$R_3$, $R_4$ and $R_5$ are identical or different from each other and represent hydrogen, saturated or unsaturated $C_1$–$C_6$ linear or branched alkyl, $C_3$–$C_7$ cycloalkyl, phenyl or aryl, or $NR_3R_4R_5$ is a saturated or unsaturated 5–7 term nitrogen heterocyclic compound optionally containing at least one additional eteroatom chosen from O, S, N, the latter being optionally substituted with a $C_1$–$C_4$ alkyl, aryl, benzyl residue, said nitrogen heterocyclic compound being optionally benzocondensed and/or substituted with $C_1$–$C_4$ alkyl, $C_1$–$C_4$ alcoxyl, $C_1$–$C_4$ alkylthio, benzyl or aryl;
L represents a heterocyclic ligand containing at least two nitrogen atoms whose electron pairs are involved in the bond with the two ruthenium atoms present in the complex, with the proviso that when said nitrogen atoms are not contained on the same heterocyclic ring L is B'—X—B", B' and B" being nitrogen heterocyclic compounds and X being chosen from the group consisting of —COO—, —O—, —$(CH_2)_n$—, —$(CH=CH)_n$—, -$(aryl)_n$-, -(heterocyclic compound)$_n$-, —CH=CH-Phe-C H=CH—, —$(C\equiv C)_n$—, with n between 0 and 4, with the proviso that when p=0 it is not $M=SO(CH_3)_2$ or $M=SO(CH_2CH_3)_2$.

2. A complex as claimed in claim 1, wherein A is Cl⁻.

3. A complex as claimed in claim 1 wherein M is chosen from the group consisting of dimethylsulphoxide, diethylsulphoxide, tetramethylenesulphoxide.

4. A complex as claimed in claim 1 wherein P is chosen from the group consisting of imidazole, N-methylimidazole, pyrazole, oxazole, pyridine, 3,5-lutidine and 4-methyl-pyridine, azepine, diazepine and oxazepine, indazole, isoquinoline, benzimidazole and 1,5,6-trimethyl-benzimidazole.

5. A complex as claimed in claim 1 wherein the heterocyclic compounds contained in B'—X—B" are heteroaromatic compounds.

6. A complex as claimed in claim 5 wherein the heteroaromatic and/or aromatic rings of said heteroaromatic compounds are substituted with a group chosen from $C_1$–$C_6$ alkyl, $C_1$–$C_4$ alkoxy, phenyl groups, CN and $NO_2$.

7. A complex as claimed in claim 5 wherein the heteroaromatic and/or aromatic rings of said heteroaromatic compounds are non-condensed.

8. A complex as claimed in claim 7 wherein said non-condensed heteroaromatic rings are chosen from the group consisting of pyrrole, imidazole, pyrazole, imidazole, pyrazole, pyrazine, pyrimidine, pyridine.

9. A complex as claimed in claim 8 wherein B'—X—B" is chosen from the group consisting of 4,4'bipyridyl, bisimidazole, 1,2-bis(4pyridyl)ethane and trans-1,2-bis (4-pyridyl)ethylene.

10. A complex as claimed in claim 5 wherein the heteroaromatic and/or aromatic rings of said heteroaromatic compounds are condensed.

11. A complex as claimed in claim 10 wherein said condensed heteroaromatic rings are chosen from the group consisting of quinoline, isoquinoline, carbazole.

12. A complex as claimed in claim 11 wherein said condensed aromatic rings are chosen from the group consisting of naphtalene, anthracene and phenantrene.

13. A complex as claimed in claims 1 wherein said hetroaromatic and/or aromatic rings of said heteroaromatic compounds are substituted with a group chosen from $C_1$–$C_6$ alkyl, $C_1$–$C_4$ alkoxy, phenyl groups, CN and $NO_2$.

14. A complex as claimed in claim 1 wherein said hetroaromatic and/or aromatic rings of said heteroaromatic compounds are is condensed.

15. A complex as claimed in claim 14 wherein said condensed aryl is chosen from the group consisting of naphtalene, anthracene and phenanthrene.

16. A salt of an anionic complexes as claimed in claim 1, where Q is chosen from the group consisting of protons bound to bases, cations of an alkaline or alkaline-earth metal, cations of formula $^+NR_3R_4R_5R_6$ where $R_3,R_4,R_5,R_6$ are identical or different from each other and represent hydrogen, saturated or unsaturated $C_1$–$C_6$ linear or branched alkyl, $C_3$–$C_7$ cycloalkyl, phenyl or aryl, or the cation $^+NR_3R_4R_5R_6$ is a saturated or unsaturated 5–7 term nitrogen heterocyclic compound, optionally containing at least one additional eteroatom chosen from O, S, N, the latter being optionally substituted with a $C_1$–$C_4$ alkyl, aryl or benzyl residue, said nitrogen heterocyclic compound being optionally benzocondensed and/or substituted with $C_1$–$C_4$ alkyl, $C_1$–$C_4$ alkoxyl, $C_1$–$C_4$ alkylthio, benzyl or aryl.

17. A salt of an anionic complexes as claimed in claim 16, wherein the cation is chosen from the group consisting of $(Me_2SO)_2H^+$, $Na^+$, $K^+$, $NH_4^{30}$, $Net_4^+$(tetraethylammonium), $Nbu^+$ (tetrabutylammonium) and $ImH^+$ (imidazole).

18. A salt of an anionic complexes as claimed in claim 1 wherein $P=NR_3R_4R_5$ and $Q=NR_3R_4R_5R_6$, with $R_6$=H.

19. A salt of an anionic complex as claimed in claim 1, wherein A=Cl, P=imidazole, W=NO, a=4, m=0, p=1, r=−1.

20. Process for the preparation of complexes as claimed in claim 1, comprising the step of dissolving in a suitable organic solvent or mixture of organic solvents a complex of formula $[Ru^{III}A_4M_2]^{-1}$ or $[Ru^{III}A_3M_3]$, adding gaseous nitrogen oxide for a period of time between 15 minutes and 5 hours and allowing the reaction to run for a time period between 30 min and 24 hours, at a temperature between 0 and 200° C. to obtain a complex of formula $[Ru^{II}A_4M_1W]^{-1}$ or $[Ru^{II}A_3M_2W]$, further reacting the complex of formula $[Ru^{II}A_4M_1W]^{-1}$ or $[Ru^{II}A_3M_2W]$ with P in a suitable organic solvent or mixture of organic solvents for a period of time between 15 min and 5 hours and at the temperature of between 0 and 150° C. to obtain a complex formula $[RuA^4P_1W]^{-1}$ or $[RuA_3M_1P_1W]$.

21. Process as claimed in claim 20 wherein said complex is reacted with P for a period of time between 1 and 4 hours.

22. Process as claimed in claim 20, further comprising the step of reacting in a suitable organic solvent or mixture of organic solvents the complex $[Ru^{II}A_4M_1W]^{-1}$ or $[Ru^{II}A_3M_2W]$ with ½ equivalent of L to obtain formula $[(RuA^4W)_2L]^{-2}$ or $[(RuA_3M_1W)_2L]$.

23. A neutral ruthenium (II) complexes of formula (I) or salt of an anionic ruthenium complex of formula (I) with cations Q for treating a human in a need thereof:

$$[RuA_aM_mP_pW]^r \qquad (I)$$

wherein:
A represents a halogen chosen form the group consisting of CF⁻and Br⁻
W represents NO⁺
M represents $SOR_1R_2$
P represents $NR_3R_4R_5$, or $LRuA_aM_mW$
a is a whole number between 3 and 4
m is a whole number between 0 and 2
p is 1 except
r can be 0, −1, −2
being a+m+p=5
wherein:

$R_1$ and $R_2$ are identical or different from each other and represent $C_1$–$C_6$ alkyl, $C_3$–$C_7$ cycloalkyl, phenyl or aryl, or $R_1$ and $R_2$ form a 5–7 term heterocyclic ring together with the sulphur atom;

$R_3$, $R_4$ and $R_5$ are identical or different from each other and represent hydrogen, saturated or unsaturated $C_1$–$C_6$ linear or branched alkyl, $C_3$–$C_7$ cycloalkyl, phenyl or aryl, or $NR_3R_4R_5$ is a saturated or unsaturated 5–7 term nitrogen heterocyclic compound optionally containing at least one additional eteroatom chosen from O, S, N, the latter being optionally substituted with a $C_1$–$C_4$ alkyl, aryl, benzyl residue, said nitrogen heterocyclic compound being optionally benzocondensed and/or substituted with $C_1$–$C_4$ alkyl, $C_1$–$C_4$ alcoxyl, $C_1$–$C_4$ alkylthio, benzyl or aryl;

L represents a heterocyclic ligand containing at least two nitrogen atoms whose electron pairs are involved in the bond with the two ruthenium atoms present in the complex, with the proviso that when said nitrogen atoms are not contained on the same heterocyclic ring L is B'—X—B", B' and B" being nitrogen heterocyclic compounds and X being chosen from the group consisting of —COO—, —O—, —$(CH_2)_n$—, —$(CH=CH)_n$—, -$(aryl)_n$-, -(heterocyclic compound)$_n$-, —CH=CH-Phe-CH=CH—, —$(C≡C)_n$—, with n between 0 and 4.

24. A complex as claimed in claim 23, wherein A is $Cl^{31}$.

25. A complex as claimed in claim 23 wherein M is chosen from the group consisting of dimethylsulphoxide, diethylsulphoxide, tetramethylenesulphoxide.

26. A complex as claimed in claim 23 wherein P is chosen from the group consisting of imidazole, N-methylimidazole, pyrazole, oxazole, pyridine, 3,5-lutidine and 4-methyl-pyridine, azepine, diazepine and oxazepine, indazole, isoquinoline, benzimidazole and 1,5,6-trimethyl-benzimidazole.

27. A complex as claimed in claim 23 wherein the heterocyclic compounds contained in B'—X—B" are heteroaromatic compounds.

28. A complex as claimed in claim 27 wherein the heteroaromatic and/or aromatic rings of said heteroaromatic compounds are substituted with a group chosen from $C_1$–$C_6$ alkyl, $C_1$–$C_4$ alkoxy, phenyl groups, CN and $NO_2$.

29. A complex as claimed in claim 27 wherein the heteroaromatic and/or aromatic rings of said heteroaromatic compounds are non-condensed.

30. A complex as claimed in claim 29 wherein said non-condensed heteroaromatic rings are chosen from the group consisting of pyrrole, imidazole, pyrazole, pyrazine, pyrimidine, pyridine.

31. A complex as claimed in claim 30 wherein B'—X—B" is chosen from the group consisting of 4,4'bipyridyl, bis-imidazole, 1,2-bis(4pyridyl)ethane and trans-1,2-bis (4-pyridyl)ethylene.

32. A complex as claimed in claim 27 wherein the heteroaromatic and/or aromatic rings of said heteroaromatic compounds are condensed.

33. A complex as claimed in claim 32 wherein said condensed heteroaromatic rings are chosen from the group consisting of quinoline, isoquinoline, carbazole.

34. A complex claimed in claim 33 wherein said condensed aromatic rings are chosen from the group consisting of naphtalene, anthracene and phenantrene.

35. A complex as claimed in claim 23 wherein said aryl contained in B'—X—B" is substituted with a group chosen from $C_1$–$C_6$ alkyl, $C_1$–$C_4$ alkoxy, phenyl groups, CN and $NO_2$.

36. A complex as claimed in claim 23 wherein said aryl contained in B'—X—B" is condensed.

37. A complex as claimed in claim 36 wherein said condensed aryl is chosen from the group consisting of naphtalene, anthracene and phenanthrene.

38. A salt of an anionic complexes as claimed in claim 23, where Q is chosen from the group consisting of protons bound to bases, cations of an alkaline or alkaline-earth metal, cations of formula $^{30}NR_3R_4R_5R_6$ where $R_3,R_4,R_5,R_6$ are identical or different from each other and represent hydrogen, saturated or unsaturated $C_1$–$C_6$ linear or branched alkyl, $C_3$–$C_7$ cycloalkyl, phenyl or aryl, or the cation $^{30}NR_3R_4R_5R_6$ is a saturated or unsaturated 5–7 term nitrogen heterocyclic compound, optionally containing at least one additional eteroatom chosen from O, S, N, the latter being optionally substituted with a $C_1$–$C_4$ alkyl, aryl or benzyl residue, said nitrogen heterocyclic compound being optionally benzocondensed and/or substituted with $C_1$–$C_4$ alkyl, $C_1$–$C_4$ alkoxyl, $C_1$–$C_4$ alkylthio, benzyl or aryl.

39. A salt of an anionic complex as claimed in claim 38, wherein the cation is chosen from the group consisting of $(Me_2SO)_2H^+$, $Na^{30}$, $K^{30}$, $NH_4^+$, $Net_4^+$(tetraethylammonium), $Nbu^+$(tetrabutylammonium) and $ImH^{30}$ (imidazole).

40. A salt of an anionic complex as claimed in claim 23 wherein $P=NR_3R_4R_5$ and $Q=NR_3R_4R_5R_6$ with $R_6=H$.

41. A salt of an anionic complexes as claimed in claim 23, wherein A=Cl, P=imidazole, W=NO, a=4, m=0, p=1, r=1.

42. A complex as claimed in claim 23 with cytostatic effect.

43. A complex as claimed in claim 23 for treating tumours and hyperproliferative pathologies.

44. A pharmaceutical composition comprising a therapeutically effective amount of at least one complex as claimed in claim 23 in combination with a pharmaceutically acceptable excipient and diluent.

45. A composition as claimed in claim 44 with cytostatic effect.

46. A composition as claimed in claim 44 for treating tumours and hyperproliferative pathologies.

* * * * *